(12) United States Patent
Xiang et al.

(10) Patent No.: US 8,846,752 B2
(45) Date of Patent: Sep. 30, 2014

(54) ISOFLAVONE FATTY ACID ESTER DERIVATIVES, PREPARATION METHOD AND PHARMACEUTICAL USES THEREOF

(75) Inventors: Hua Xiang, Jiangsu (CN); Wei Zhao, Jiangsu (CN); Hong Xiao, Jiangsu (CN); Yao Yao, Jiangsu (CN); Renling Ma, Jiangsu (CN); Lei Qian, Jiangsu (CN); Xiaobo Li, Jiangsu (CN); Qidong You, Jiangsu (CN); Qingjiang Liao, Jiangsu (CN)

(73) Assignees: China Pharmaceutical University, Nanjing, Jiangsu (CN); Nanjing Medical University Affiliated Brain Hospital, Nanjing, Jiangsu (CN)

( * ) Notice: Subject to any disclaimer, the term of this patent is extended or adjusted under 35 U.S.C. 154(b) by 44 days.

(21) Appl. No.: 13/582,038

(22) PCT Filed: Mar. 1, 2010

(86) PCT No.: PCT/CN2010/070808
§ 371 (c)(1),
(2), (4) Date: Dec. 14, 2012

(87) PCT Pub. No.: WO2011/106924
PCT Pub. Date: Sep. 9, 2011

(65) Prior Publication Data
US 2013/0079393 A1    Mar. 28, 2013

(51) Int. Cl.
*A61K 31/352* (2006.01)
*C07D 311/36* (2006.01)

(52) U.S. Cl.
CPC ............ *C07D 311/36* (2013.01); *A61K 31/352* (2013.01)
USPC .......................................... 514/456; 549/403

(58) Field of Classification Search
USPC .......................................... 514/456; 549/403
See application file for complete search history.

(56) References Cited

PUBLICATIONS

Guo et al. (Nutrition Research 29 (2009) 656-663).*

* cited by examiner

*Primary Examiner* — Noble Jarrell
*Assistant Examiner* — Valerie Rodriguez-Garcia
(74) *Attorney, Agent, or Firm* — Tianhua Gu; Global IP Services

(57) ABSTRACT

Isoflavone fatty acid ester derivatives of formula (I) or (II), the preparation method thereof and the pharmaceutical compositions containing such compounds are disclosed. The uses of such compounds in preparation of medicaments for preventing or treating hyperlipidemia, obesity or type II diabetes are also disclosed.

10 Claims, 2 Drawing Sheets

ISOFLAVONE FATTY ACID ESTER DERIVATIVES, PREPARATION METHOD AND PHARMACEUTICAL USES THEREOF

CROSS REFERENCE TO RELATED PATENT APPLICATION

The present application is the US national stage of PCT/CN2010/070808 filed on Mar. 1, 2010, which claims the priority of PCT/CN2010/070808 filed on Mar. 1, 2010, which application is incorporated herein by reference.

FIELD OF INVENTION

The present invention relates to the field of pharmaceutical chemistry, specially involving the isoflavone fatty acid ester derivatives. The present invention also discloses their preparation method and pharmacological activities, the pharmaceutical compositions containing such compounds as well as their pharmaceutical uses, especially the uses for preventing or treating hyperlipidemia, obesity or type II diabetes.

RELATED ART

As one of the most common chronic endocrine and metabolic diseases, obesity, showing an increasing trend in the incidence in today's population, has become a global public health problem. Obesity can lead to many health problems, not only increasing the morbidity and mortality of hyperlipidemia, hypertension, coronary heart disease and type II diabetes, but also easy to cause respiratory complications, osteoarthritis disease and mental illnesses. Various experimental results show that moderate weight loss (5-10%) can significantly reduce the risk factor for diabetes, cancer and cardiovascular system.

The causes of obesity are very complex, involving the interaction of genetic, environmental, psychological, behavioral and other factors. Obesity is usually treated by comprehensive measures, including dietotherapy, kinesitherapy, behavior therapy, surgical therapy and pharmacotherapy. Pharmacotherapy is a useful choice in case of inefficiency of the former several therapies or high recurrence rate. There are many types of slimming drugs, most of which are still in clinical or pre-clinical research stage. According to the mechanism of action, the drugs can be divided into three categories: ①drugs to subdue appetite, usually acting on the central nervous system or peripheral nervous to reduce food intake by affecting appetite; ②drugs to inhibit intestinal canal digestion and absorption, mainly acting on the gastrointestinal tract to reduce the energy absorption; ③drugs to increase energy consumption, acting on the metabolic process to accelerate the consumption of energy. In the above three types of drugs, only Sibutramine and Orlistat are the slimming drugs that are approved by FDA and can be used long-term. As a 5-hydroxytryptamine reuptake inhibitor, Sibutramine acts on the central nervous system to reduce food intake by enhancing satiety and improving the metabolic rate. As a lipase inhibitor, Orlistat can prevent food fat absorption in the intestines. Although both of these are allowed to use in long term, there are still some side effects: the former easily causes blood pressure elevation and cardiac arrythmias, while the latter will lead to greasy stool, fat-soluble vitamin malabsorption and colonic damage. Therefore, safer slimming drugs with new mechanism of action shall be researched and sought.

The metabolic syndrome (MS) caused by obesity, especially by central obesity has become a health killer in modern society. It generally refers to a syndrome that obesity, type II diabetes, hyperlipidemia, hypertension and other pathological phenomena are gathered in a body. As one of nuclear receptor superfamily members of transcription factor and the main regulator for adipocyte gene expression and signal transduction between insulin cells, peroxisome proliferators activated receptor γ (PPARγ) is mainly expressed in adipose tissue and plays an important role in regulating adipocyte differentiation, glucose uptake and fatty acid metabolism. After activated, PPARγ has the roles of promoting adipocyte differentiation, adjusting fat deposition, improving insulin sensitivity, regulating body sugar and lipid balance and reducing inflammation. As the insulin sensitizers used in the PPARγ agonist to treat diabetes, thiazolidinediones (TZDs) drugs can significantly improve the insulin resistance of patients with type II diabetes. However, due to weight gain, fluid retention, edema, congestive heart failure and other side effects, the clinical application of TZDs drugs is much limited.

Oleoyl-estrone (OE) is a naturally existing endogenous acyl-estrone compound, which, in pre-clinical animal study results, has a significant weight loss effect without impacted by changes in diet. Meanwhile, it also has a significant role in depressing blood fat and regulating blood sugar balance. OE is dissolved in vegetable oil or is prepared as a lipidosome for administration. The effect of oral administration is better than intravenous injection.

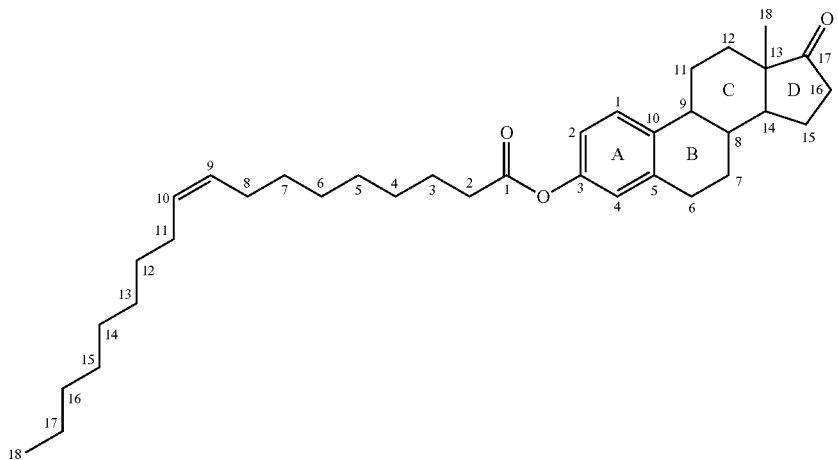

Structural formula of Oleoyl-estrone

OE is the main existence form of animal endogenous estrone. When the cells are full of fat, the adipose tissue (mainly white adipose tissue) will synthesize OE and send signals to the brain to reduce appetite. This function is much similar to leptin. The results of animal experimental research conducted by American Manhattan Pharmaceuticals show that the action mechanism of OE lies in maintaining the balance between OE and estrone in blood plasma rather than directly related to the release of estrone. High estrone level is conductive to fat deposition; the physical environment of low amount of fat contributes OE to be transformed into estrone. The estrone level in plasma of obese animals is relatively high and long-term high estrone level easily breaks the balance between OE and estrone, so that the adipocyte in the body cannot produce enough high-level OE to notify the hypothalamus weight regulator (Ponderostat) to suppress appetite in order to lose weight. The experiments of SD rats confirm that OE weight-losing effect depends on the dose. No significant changes in body protein content are found in oral administration experiments. One hour after OE is marked, OE content in the hypothalamus is measured to be much higher than its content in blood, liver and white adipose tissue. This result supports the inference that OE is considered as the "weight regulatory signal". During oral administration, OE is mostly absorbed in the body in the form of original drug, but there is still 17% absorbed in free estrone form and 12% absorbed in estrone water-soluble ester. The half-life of intravenous injection is 250 s and the half-life of oral administration has not been measured (Cullell-Young M. Drugs of Future, 2002, 27 (7): 648-654). After completing Phase IIa clinical research for OE treatment of obesity, Manhattan Pharmaceuticals announced the termination of further research (www.manhattanpharma.com/7K 2007-7-9).

SUMMARY OF THE INVENTION

The present invention discloses type I isoflavone fatty acid ester derivatives of general formula I or general formula II. The preliminary animal studies show that the compounds in the present invention have the role of depressing blood fat and losing weight for obese rats, and also have certain effect of scavenging free radicals, resisting oxidative damage, reducing insulin resistance and regulating blood sugar balance. During in vitro experiments, part of the compounds in the present invention can significantly inhibit preadipocyte differentiation and proliferation and can activate the expression of PPARγ2-mRNA.

The structural formulas of the compounds in the present invention are as follows:

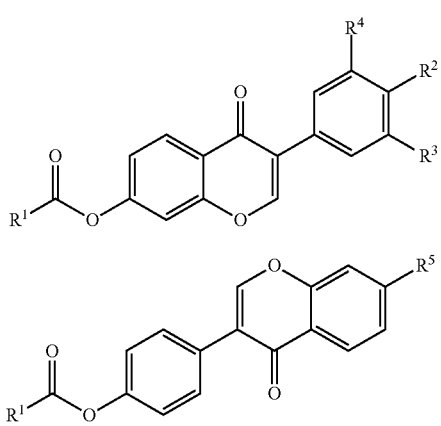

$R^1CO$ represents: $C_{11}$-$C_{30}$ fatty acyl groups. The fatty acyl group is formed by $C_{11}$-$C_{30}$ saturated or unsaturated fatty acid after removal of hydroxide radical;

$R^2$, $R^3$ and $R^4$ independently represent H, OH, OR', SR', NHR', N(CH$_3$)$_2$, NO$_2$, halogen, CF$_3$ or C(O)R' respectively, in which, R' represents $C_1$-$C_4$ alkyl group and when $R^3$ and $R^4$ represents H at the same time, $R^2$ does not represent OH;

$R^5$ represents H, OR', SR', NHR', N(CH$_3$)$_2$, NO$_2$, halogen, CF$_3$ or C(O)R', in which, R' represents $C_1$-$C_4$ alkyl group;

When $R^4$ represents H, $R^2$ and $R^3$ can form

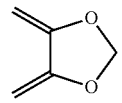

with their combined carbon atom.

The above $R^1CO$ preferred represents the fatty acyl group formed by oleic acid, linoleic acid, undecylenic acid, linolenic acid, conjugated linoleic acid, stearic acid, palmitoleic acid, eicosatetraenoic acid, eicosapentaenoic acid, eicosenoic acid, docosahexaenoic acid, lauric acid, capric acid, octanoic acid or hydroxy-2-decenoic acid after removal of hydroxide radical.

$R^1CO$ more preferred represents oleoyl, linoleoyl, linolenic acyl, conjugated linoleoyl or palmitoleic acyl.

$R^2$ preferred represents H, OH, OCH$_3$, SCH$_3$, NHCH$_3$, N(CH$_3$)$_2$, NO$_2$, halogen, CF$_3$ or C(O)CH$_3$.

$R^2$ more preferred represents OCH$_3$.

$R^3$ and $R^4$ preferred represent H, OH or OCH$_3$.

$R^3$ and $R^4$ more preferred represent H.

Some compounds in the present invention are as follows:

4'-methoxy-7-O-oleoyl daizeol (code: I-1, the same below)
4'-methoxy-7-O-linoleoyl daizeol (I-2)
4'-methoxy-7-O-stearoyl daizeol (I-3)
4'-methoxy-7-O-palmityl daizeol (I-4)
4'-methoxy-7-O-undecylenoyl daizeol (I-5)
3',4'-dimethoxy-7-O-oleoyl daizeol (I-6)
7-methoxy-4'-O-oleoyl daizeol (II-1)
7-methoxy-4'-O-linoleoyl daizeol (II-2)
7-methoxy-4'-O-stearoyl daizeol (II-3)
7-methoxy-4'-O-palmityl daizeol (II-4)
7-methoxy-4'-O-undecylenoyl daizeol (II-5)

The codes of the compounds in the following pharmacological experiments are equivalent to the structures of the compounds corresponded by the codes here.

The compounds in general formulas I and II of the present invention can be prepared by the following method:

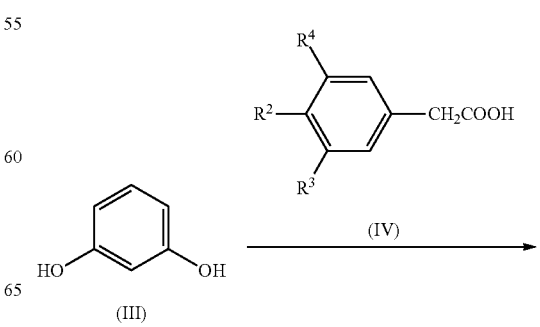

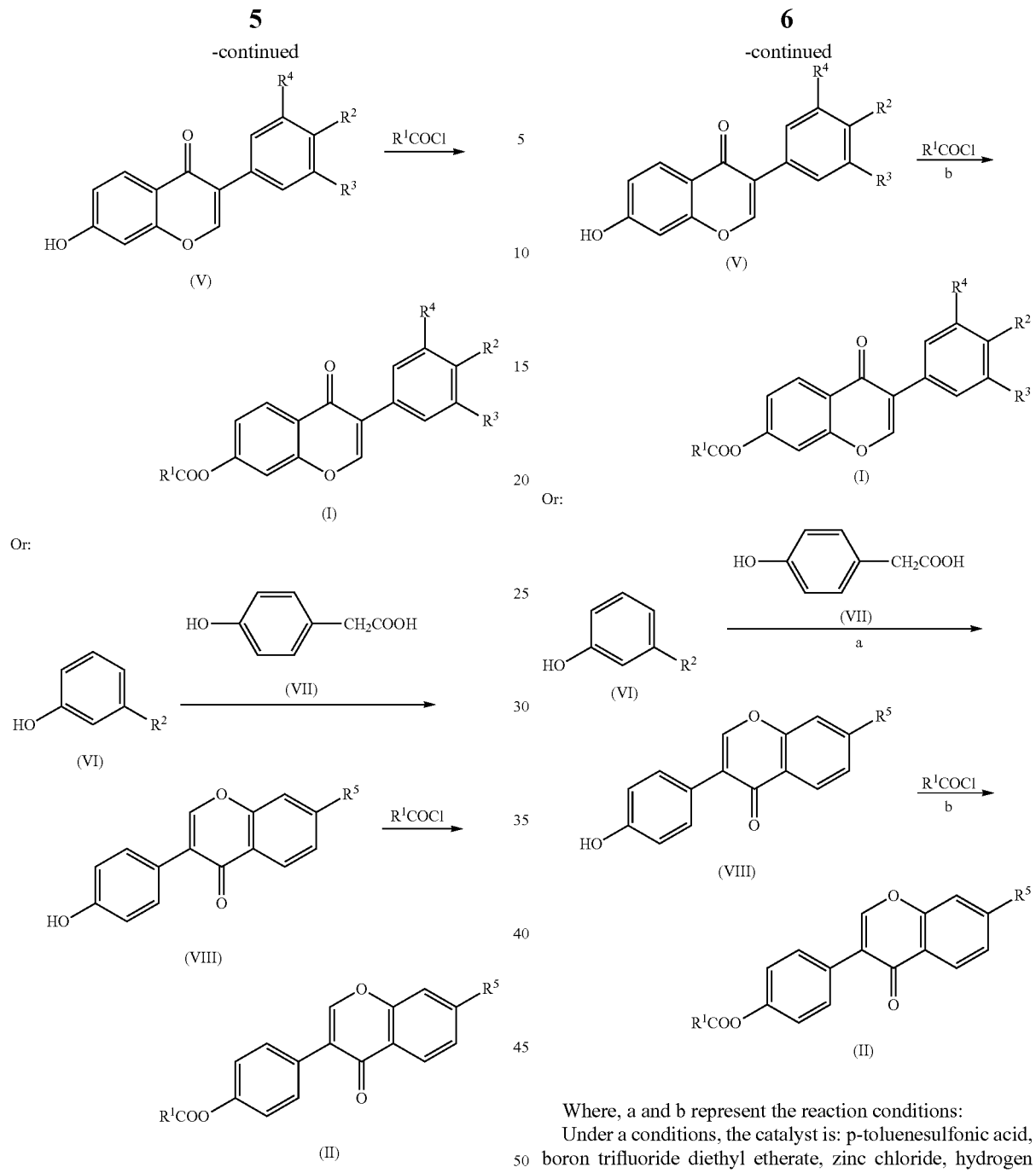

The more preferred preparation method is:

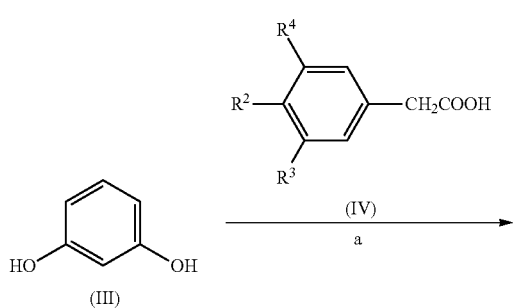

Where, a and b represent the reaction conditions:

Under a conditions, the catalyst is: p-toluenesulfonic acid, boron trifluoride diethyl etherate, zinc chloride, hydrogen chloride gas, triethyl orthoacetate, hexahydropyridine, N,N-dimethyl formamide dimethyl acetal, phosphorus trichloride, phosphorus pentachloride, phosphorus oxychloride or methylsulfonyl chloride.

The reaction solvent is: boron trifluoride diethyl etherate, diethyl ether, N,N-dimethyl formamide, dimethyl sulfoxide, benzene, toluene, methanol, ethanol, pyridine, ethyl formate, ethyl acetate or the mixed solvent of two or above of above-mentioned solvents. The reaction temperature is 15 to reflux.

Under b conditions, the catalyst is: pyridine, sodium hydride, potassium hydride, alkali hydride, potassium tert-butoxide, sodium hydroxide or potassium hydroxide.

The reaction solvent is: dichloromethane, chloroform, N,N-dimethyl formamide, dimethyl sulfoxide, pyridine, benzene, toluene or the mixed solvent of two or above of above-mentioned solvents.

The reaction temperature is room temperature to reflux.

The followings are some pharmacological experiments and results of some compounds in the present invention:

1. Activity Determination of Losing Weight and Depressing Blood Fat of SD Rats

The experiment refers to the methods in *Experimental Methodology of Pharmacology* compiled by Xu Shuyun et al, People's Medical Publishing House 2002: 1189-1201, which is slightly modified.

1.1 Experimental Methods

SD rates (weight 80 g-100 g, male, clean grade) are randomly divided into the following groups according to the weight:

Blank control group (normal diet group); model control group (high-fat diet group); sibutramine, 1.0 mg/kg; Group I-1, 25 mg/kg; Group I-2, 25 mg/kg; Group I-3, 25 mg/kg; Group II-1, 25 mg/kg; Group II-2, 25 mg/kg; Group II-3, 25 mg/kg.

Except the blank control group, the other groups are fed with high-fat diet for two months. In the third month, all groups are required for intragastric administration and the blank control group and model control group are given appropriate volume of excipients once a day for a consecutive month. After the administration, exsanguinate and kill the rats, take femoral arterial blood and separate the plasma, and then measure the parameters according to the unified operating procedures in the kit instructions. Remove the fat around abdominal cavity and reproductive organs, weigh its wet weight and determine the body weight.

1.2 Experimental Results

The compounds of the present invention can significantly reduce serum total cholesterol (TC), triglyceride (TG), free fatty acid (FFA), fax index and body fat mass.

insulin (0.5 U/kg) each day. The food is not restricted. Measure the food regularly each day, weigh the weight once a week and feed 7 consecutive weeks.

2.1.2 Experimental Treatment:

7 weeks after modeling, the normal diet group is unchanged and the high fat and high sugar model group is divided into model control group (n=10), I-1 administration group (n=10) and I-2 administration group (n=10). The feed of each group is unchanged. The administration group is given corresponding compounds with the dose of 50 mg/kg and the blank group is given the equal volume of blank solvent. Conduct intragastric administration on each group for consecutive 30 days. Weigh 12 h after fasting after last administration, take the eyeballs for blood, prepare serum, determine the blood fat (triglyceride TG, free fatty acid FFA, total cholesterol TC, low density lipoprotein cholesterol LDL-C and high density lipoprotein cholesterol HDL-C) content and blood insulin content and detect the oxidative damage indicators in the blood (malondialdehyde MAD and superoxide dismutase SOD). Take off the cervical vertebrae to kill the rats, separate the perirenal, testicular, mesenteric and inguinal (subcutaneous) white adipose tissue, wash clean with cold physiological saline and dry with filter paper, and then weigh.

2.2 Experimental Results

The compounds of the present invention can significantly reduce the body weigh and body fat weight of the obese rats and can also improve blood fat level, reduce serum insulin concentration, enhance SOD activity and reduce MDA content, indicating that they can eliminate the free radicals in the body.

TABLE 1

Impact of some Series I Compounds on Body Weight and Blood Fat of High Fat Diet Rats (mean ± SD, n = 10)

| | Weight after administration (g) | Fat index (g/100 g) | Triglyceride TG (mmol/l) | Total cholesterol TC (mmol/l) | Free fatty acid FFA (μmol/l) |
|---|---|---|---|---|---|
| Blank control group | 275 ± 34 | 4.6 ± 1.9 | 0.61 ± 0.16 | 1.44 ± 0.19 | 604.2 ± 57.4 |
| Model control group | 355 ± 36## | 6.4 ± 1.4## | 1.25 ± 0.23## | 1.86 ± 0.31## | 785.6 ± 175.8 |
| Sibutramine group | 301 ± 41* | 4.3 ± 1.7* | 0.97 ± 0.31* | 1.32 ± 0.29* | 609.6 ± 138.3* |
| Group I-1 | 309 ± 36* | 5.0 ± 1.6* | 0.91 ± 0.22* | 1.31 ± 0.27** | 606.7 ± 144.7* |
| Group I-2 | 307 ± 32* | 4.3 ± 1.5* | 0.99 ± 0.21* | 1.28 ± 0.26** | 603.8 ± 163.5* |
| Group I-3 | 320 ± 34 | 5.4 ± 1.2 | 1.19 ± 0.30 | 1.57 ± 0.30 | 730.2 ± 186.0 |
| Group II-1 | 328 ± 32 | 5.6 ± 1.6 | 1.01 ± 0.24* | 1.65 ± 0.25 | 696.3 ± 205.4* |
| Group II-2 | 318 ± 28 | 5.1 ± 1.3* | 1.03 ± 0.21* | 1.67 ± 0.23 | 658.8 ± 201.2* |
| Group II-3 | 352 ± 47 | 6.0 ± 2.1 | 1.35 ± 0.35 | 1.71 ± 0.34 | 738.1 ± 196.0 |

The data are represented by mean ± standard deviation. The variance analysis and t-test are conduced for all groups of data.
*P < 0.05, **P < 0.01, compared with the model control group;
P < 0.05, ##P < 0.01, compared with blank control group.

2. Activity Determination of Losing Weight, Depressing Blood Fat and Regulating Blood Sugar Balance of ICR Mice The experiment refers to the methods of Raquel Ferrer-Lorente et al (European Journal of Pharmacology, 2005, 513: 243-248), which are slightly modified.

2.1 Experimental Methods 2.1.1 Modeling Method:

Take 40 ICR mice (male, weight 13-15 g) and randomly divide them into two large groups according to their weight, a normal diet group (n=10) and a high fat and high sugar model group (n=30); give normal diet to the normal diet group and conduct subcutaneous injection of physiological saline each day; give high-fat and high-sugar diet to the high fat and high sugar model group and conduct subcutaneous injection of

TABLE 2

Changes in Body Weight of Mice before and after Administration (n = 10, x̄ ± s)

| | Before administration (g) | 1 week after (g) | 2 weeks after (g) | 3 weeks after (g) |
|---|---|---|---|---|
| Normal blank group | 32.1 ± 1.6 | 33.0 ± 2.3 | 31.3 ± 1.8 | 32.9 ± 3.1 |
| Model control group | 42.4 ± 5.5## | 41.2 ± 5.5## | 37.6 ± 3.7## | 37.9 ± 1.8# |

TABLE 2-continued

Changes in Body Weight of Mice before and after Administration (n = 10, $\bar{x} \pm s$)

| | Before administration (g) | 1 week after (g) | 2 weeks after (g) | 3 weeks after (g) |
|---|---|---|---|---|
| Group I-1 | 41.8 ± 5.7 | 39.1 ± 5.2 | 33.8 ± 3.7* | 31.5 ± 2.0** |
| Group I-2 | 42.0 ± 4.4 | 39.1 ± 4.1 | 32.9 ± 5.7* | 29.5 ± 2.3** |

P < 0.05, ##P < 0.01, compared with normal blank group;
*P < 0.05, **P < 0.01, compared with high fat blank group

TABLE 3

Impact of Body Fat Weight of Mice after Administration (n = 10, $\bar{x} \pm s$)

| | Epididymal fat (g) | Perirenal fat (g) | Mesenteric fat (g) | Celiac total fat (g) | Subcutaneous fat (g) |
|---|---|---|---|---|---|
| Normal bland group | 0.339 ± 0.077 | 0.131 ± 0.079 | 0.192 ± 0.042 | 0.662 ± 0.117 | 0.145 ± 0.045 |
| Model control group | 0.804 ± 0.161## | 0.245 ± 0.079## | 0.244 ± 0.024## | 1.292 ± 0.226## | 0.294 ± 0.116## |
| Group I-1 | 0.382 ± 0.230** | 0.078 ± 0.050** | 0.135 ± 0.047** | 0.595 ± 0.172** | 0.136 ± 0.065* |
| Group I-2 | 0.212 ± 0.239** | 0.059 ± 0.057** | 0.058 ± 0.101** | 0.329 ± 0.403** | 0.099 ± 0.071** |

P < 0.05, ##P < 0.01, compared with normal blank group;
*P < 0.05, **P < 0.01, compared with high fat blank group

TABLE 4

Changes in Blood Fat Indicators of Mice after Administration (n = 10, $\bar{x} \pm s$)

| | TG (mmol/l) | FFA (mmol/l) | TC (mmol/l) | LDL-C (mmol/l) | HDL-C (mmol/l) |
|---|---|---|---|---|---|
| Normal bland group | 1.78 ± 0.21 | 0.89 ± 0.15 | 3.13 ± 0.27 | 1.174 ± 0.460 | 1.53 ± 0.22 |
| Model control group | 1.67 ± 0.40 | 0.75 ± 0.20 | 4.32 ± 0.66# | 1.470 ± 0.660# | 2.21 ± 0.22# |
| Group I-1 | 0.97 ± 0.21* | 0.55 ± 0.14 | 2.79 ± 0.39** | 1.068 ± 0.636 | 1.70 ± 0.53 |
| Group I-2 | 0.71 ± 0.22** | 0.43 ± 0.04* | 3.18 ± 0.46* | 0.880 ± 0.655* | 1.56 ± 0.29* |

P < 0.05, ##P < 0.01, compared with normal blank group;
*P < 0.05, **P < 0.01, compared with high fat blank group

TABLE 5

Change in Serum Insulin Concentration of Mice after Administration (n = 10, $\bar{x} \pm s$)

| | Normal bland group | Model control group | Group I-1 | Group I-2 |
|---|---|---|---|---|
| INS (U/ml) | 25.39 ± 5.20 | 70.81 ± 47.16## | 20.26 ± 2.69** | 22.32 ± 6.39* |

P < 0.05, ##P < 0.01, compared with normal blank group;
*P < 0.05, **P < 0.01, compared with high fat blank group

TABLE 6

Changes in Serum Oxidative Damage Indicators of Mice after Administration (n = 10, $\bar{x} \pm s$)

| | Normal bland group | Model control group | Group I-1 | Group I-2 |
|---|---|---|---|---|
| SOD (U/ml) | 538.8 ± 114.1 | 608.7 ± 150.5 | 382.3 ± 200.9* | 424.1 ± 192.8 |
| MDA (nmol/l) | 0.556 ± 0.193 | 1.383 ± 0.203# | 0.810 ± 0.162* | 1.288 ± 0.145 |

P < 0.05, ##P < 0.01, compared with normal blank group;
*P < 0.05, **P < 0.01, compared with high fat blank group 3. Acute Toxicity Test of KM Mice 3.1 I-1 Acute Toxicity Test of Intragastric Administration (ig) for Mice I-1 Acute Toxicity Test Results Show that:

$LD_{50}$ value of the mice intragastric administration (ig) is 2163.8 mg/kg. Abnormal reaction of mice toxic symptoms: decrease in spontaneous activities, often creeping lying without moving, slower weight gain, animal quite to death. About 1 h after administration, the mice begin to die and the death occurs within 1~2 days after administration. Examine the postmortem of dead mice with naked eyes, no organs showing obvious pathological changes. After about 48 h, mice activities begin to increase and return to normal.

3.2 I-1 Acute Toxicity Test of Subcutaneous Injection (sc) for Mice

I-1 Acute Toxicity Test Results Show that:

After sc I-1 2000 mg/kg of mice under the conditions of maximum administration capacity and maximum administration concentration, no mice die and the mice toxic symptoms express as decrease in spontaneous activities and often creeping lying without moving. After about 48 h, mice activities begin to increase. Compared with the control group, the weight gain in subsequent observation period is slower.

4. 3T3-L1 Cell Culture Experiment 4.1 Experimental Methods 4.1.1 Cell Proliferation Determination Experiment with MTT Method Inoculate 3T3-L1 cells in 96-hole cell culture plate. After 2 d of conventional culture, replace with DMEM culture solutions with different concentrations (25, 50, 100 and 200 μmol/L) of Series I compounds. The control group is the culture solution containing 0.1% (V/V) ethanol (96%). 3 complex holes are set for each concentration in each group, processing 2 d. Discard the culture solution in the holes and add 20 μL MTT solution in each hole and culture at 37 for 4 h. Then discard the solution in the hole, add 100 μL DMSO solution in each hole, shake thoroughly and measure the absorbance (A) immediately in the enzyme-linked immunosorbent assay. The wavelength is measured to be 570 nm.

4.1.2 Oil Red Staining Colorimetric Experiment 4.1.2.1 Culture 3T3-L1 cells in conventional medium and replace with differential medium I (DMEM culture solution containing 15% FBS, 0.4 mmol/L IBMX, 10 mg/L insulin and 1 μmol/L DEX) 2 d after the cells are completely merged (0 d of differentiation) for culture for 2 d. In the second day of differentiation, replace with differential medium II (DMEM culture solution containing 15% FBS and 10 mg/L insulin) to culture cells. In the $6^{th}$ day of differentiation and later, replace with corresponding DMEM culture solution containing series I compounds. The control group is the complete culture solution without drugs.

4.1.2.2. Oil Red O Staining

In the $8^{th}$ day of differentiation, discard the culture solution in the holes, wash with PBS for twice and add the solution containing 10% methanal to fix cells for 2 h. Wash with PBS for twice and stain with 0.5% oil red for 2 h. Wash with PBS for three times, dry at 37, add isopropanol, extract for 10 min and measure the absorbance value of the extract liquor at 492 nm.

4.1.3 Reverse Transcription

Polymerase chain reaction (RT-PCR) experiment Extract the total RNA of fully differentiated 3T3-L1 cells to be reversely transcribed into cDNA. The primers are designed as follows:

```
PPARγ2 Upstream sequence:
5'-ACCACTCGCATTCCTTTGAC-3',

Downstream sequence:
5'-TCAGCGGGAAGGACTTTATG-3',
```

The length of the target product is 567 bp.

```
GAPDH Upstream sequence:
5'-GTTCCAGTATGACTCTACCC-3',

Downstream sequence:
5'-AGTCTTCTGAGTGGCAGTGATGGC-3',
```

The length of the target product is 424 bp.

PCR amplification conditions: initial denaturation at 94 for 5 min, then denaturize at 94 for 30 s, anneal at 57 for 40 s, and extend at 72 for 50 s, a total of 30 cycles. Finally extend at 72 for 10 min. Then conduct electrophoresis analysis with 1.5% agarose gel. GAPDH is used as the internal reference to alleviate the error between different samples. Compare the optical density of objective band with the optical density of amplified GAPDH band for analysis.

4.2 Experimental Results

MTT experiment shows that I-1 has significant inhibition action on the proliferation of preadipocyte 3T3-L1 (P<0.05), as shown in FIG. 1 (mother nucleus 4'-methoxy daizeol as a control, * means there are significant differences when OD value is compared with that in blank group, p≤0.05). The oil red staining colorimetric experiment results are shown in FIG. 2 and FIG. 3 (mother nucleus 4'-methoxy daizeol as a control, * means there are significant differences when the inhibition rate is compared with that in blank group, p≤0.05). In FIG. 2, A is the morphological change in normal differentiation process of 3T3-L1 cells and B is the morphological change in the differentiation process of 3T3-L1 cells after given with I-1. a, b, c and d in A respectively represent: a. low-density 3T3-L1 cell morphology before differentiation; b. in the $4^{th}$ day of differentiation, more 3T3-L1 cells have been differentiated into mature adipocytes, in which "ring shape" lipid droplets can be seen and some cells have large lipid droplets; c. in the $8^{th}$ day of differentiation, 90% cells have been differentiated into mature adipocytes, and the cells are further increased and rounded with rich cytoplasm and the cells are full of large lipid droplets; d. in the $8^{th}$ day of differentiation, the oil red is stained and a large number of "ring shape" lipid droplets can be seen. a, b, c and d in B respectively represent: a. low-density 3T3-L1 cell morphology before differentiation; b. in the $4^{th}$ day of differentiation, more 3T3-L1 cells have been differentiated into mature adipocytes, in which "ring shape" lipid droplets can be seen and there is no significant differences compared with the $4^{th}$ day of normal differentiation; c. in the $8^{th}$ day of differentiation and $2^{nd}$ day of administration, the lipid droplets are less and smaller compared with that in the $8^{th}$ day of normal differentiation; d. in the $8^{th}$ day of differentiation, the oil red is stained and the red "ring shape" lipid droplets are significantly decreased. FIG. 2 and FIG. 3 show that the compounds of the present invention have significantly role in inhibiting adipose differentiation (P<0.05).

RT-PCR results show that (FIG. 4) during the differentiation of preadipocyte 3T3-L1, PPARγ2-mRNA expression quantity is increased after the action of series I compounds I-1 and I-2 and is significantly decreased after the action of the compounds I-3 and I-4, indicating that the compounds I-1 and I-2 may exert its physiological activity by activating PPARγ. The compounds I-1 and I-2 contain unsaturated fatty acid side chains, while I-3 and I-4 contain saturated fatty acid side chains, inferring that the expression quantity of PPARγ2-mRNA is related to the structure of side chains.

5. Conclusion

Pharmacological experiments show that the compounds in the present invention, with certain weight losing and blood fat depressing activities, can slow down the weight gain of high-fat tested mice, reduce body fat weight, lower serum total cholesterol, and triglyceride and free fatty acid. Especially in I-1 and I-2, the pharmacological activity is the strongest.

Preliminary pharmacological experiments show that the compounds in the present invention can improve blood fat level, lower serum insulin concentration, enhance SOD activity and reduce MDA content, indicating that they have the roles of eliminating free radicals in the body, reducing insulin resistance and regulating blood sugar balance. The compounds also apply to type II diabetes.

In vitro experiments show that the compound I-1 of the present invention can significantly inhibit the differentiation and proliferation of adipose cells and activate the expression of PPARγ2-mRNA, indicating that it may be a selective PPARγ agonist.

Compared with thiazolidinedione drugs (insulin sensitizers), the compounds of the present invention can improve insulin sensitivity, but can also inhibit the differentiation and proliferation of adipose cells without the side effects of weight gain, developing a new direction for the research and development of drugs to treat diabetes.

The compounds of the present invention are used to prevent or treat obesity and hyperlipidemia, remove free radicals in the body, reduce insulin resistance and regulate blood sugar balance. The action mechanism, action intensity and action time need to be clarified in further study.

The present invention further involves the compounds of formula (I) or (II) and the pharmaceutical compositions composed of pharmaceutically acceptable carriers.

The compounds of the present invention can formulate the preparations separately or with one or more pharmaceutically acceptable carriers for administration. The compounds can be administered with oral formulations, such as ordinary tablets and capsules, sustained release tablets and capsules, controlled release tablets and capsules, dropping pills, dispersible powders and granular formulations, etc, and can also be prepared as injectable preparations. These pharmaceutical preparations may contain the active ingredients in combination with carriers with 0.05% to 90% by weight, the active ingredient with 15% to 60% by weight more commonly. The dose of compounds of the present invention may be 0.001-100 mg/kg/day and may also deviate from this dose range according to different disease extent or different dosage forms.

DETAILED DESCRIPTION OF PREFERRED EMBODIMENTS

Figure 1:
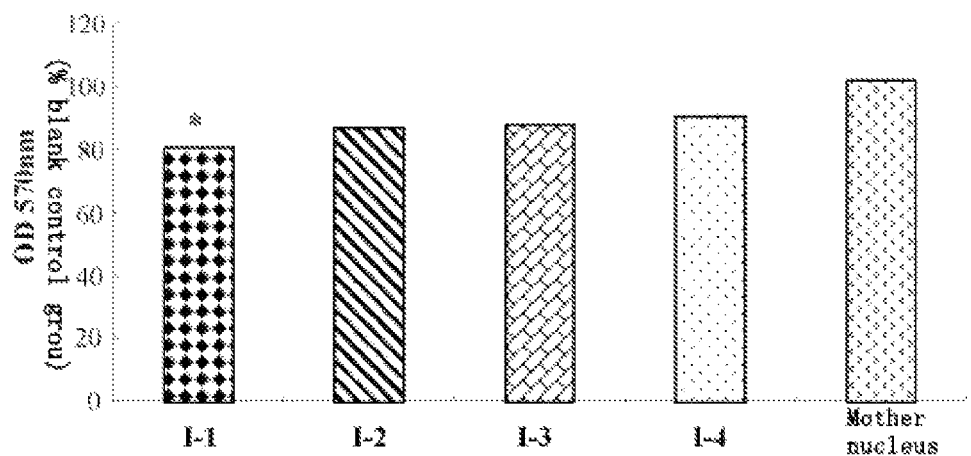
FIG. 1 Determination of the Impact of Series I Compounds on Preadipocyte Proliferation with MTT Method FIG. 2 Morphological Change in 3T3-L1 Cell Differentiation Process FIG. 3 Impact of Some Compounds of the Present Invention on Preadipocyte Differentiation Process FIG. 4 Impact of Some Compounds of the Present Invention on PPARγ2-mRNA Expression in 3T3-L1 Cells (1: bland control group, 2: I-1 (100 mmol/L), 3: mother nucleus (100 mmol/L), 4: I-2 (100 mmol/L), 5: pioglitazone (100 mmol/L), 6: I-3 (100 mmol/L), 7: I-4 (100 mmol/L).)
Figure 2:
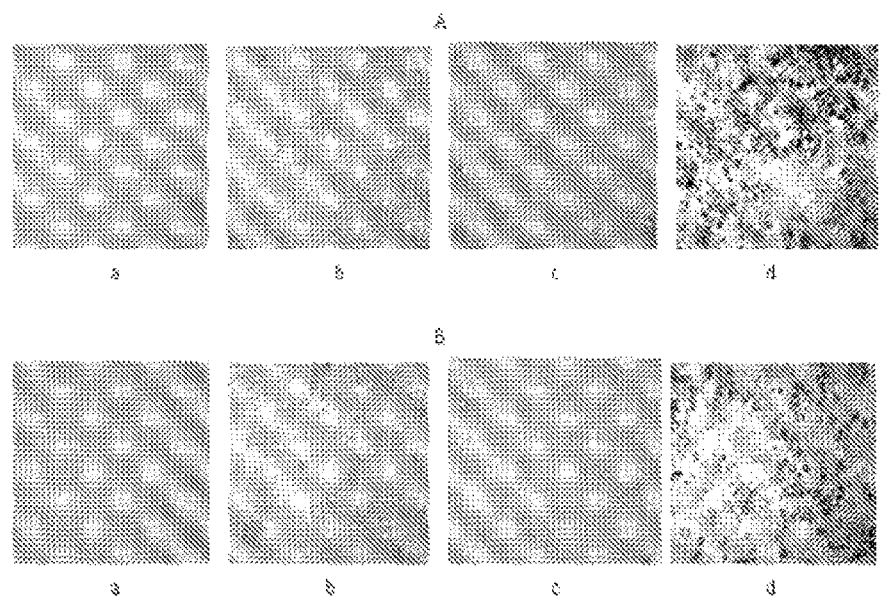
Figure 3:
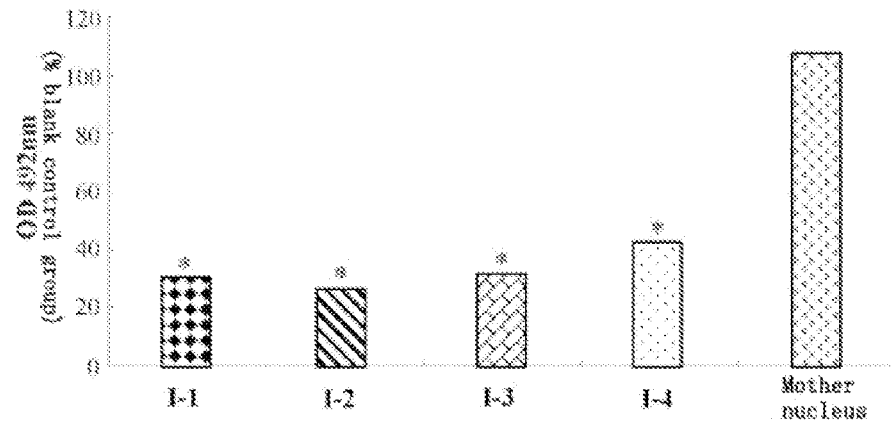
Figure 4:
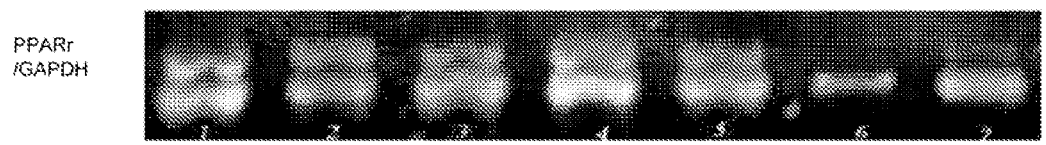
Figure 4:
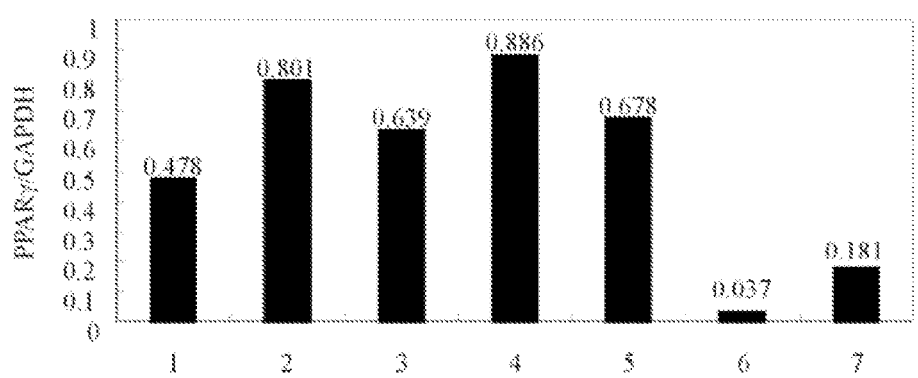

Preparation embodiments of some compounds are as follows:

For melting point, XT4 micro melting point apparatus is used; nuclear magnetic resonance hydrogen spectrometer is Bruker AV 500 type (TMS is internal standard); the mass spectrometer is Shimadzu GCMS-QP2010 mass spectrometer; the infrared spectrometer is Nicolet Impact 410 type (KBr tabletting); elemental analyzer is Elementar Vario EL III.

Embodiment 1

Preparation of 4'-methoxy daizeol

Dissolve 3.6 g resorcin (32.5 mmol) with 50 ml freshly distilled boron trifluoride diethyl etherate solution and then add 5.00 g (30.0 mmol) p-methoxy phenylacetic acid. The mixture reacts for 1 h at 100. Add 100 ml diethyl ether for dilution after cooling, extract three times with saturated sodium bicarbonate solution, add anhydrous sodium sulfate in organic phase and dry for a night. Remove the solvent by reducing pressure and concentrating, recrystallize the crude product with anhydrous ethanol and obtain 5.59 g off-white power with the productivity of 77%, mp 150-152, MS (EI) m/e: 259 [M+H]$^+$.

Take 5.16 g (20.mmol) product of above step and 4.8 g (40.0 mmol) DMF-DMA (N,N-dimethylformamide dimethyl acetal) dissolved in 60 ml anhydrous toluene, heat to reflux for 2 h, statically cool down to precipitate the solid. Recrystallize with 95% ethanol after filtration and obtain 4.02 g faint yellow product of 4'-methoxy daizeol with the productivity of 75%, mp 256-258. MS (ESI) m/e: 269 [M+H]$^+$.

Embodiment 2

Preparation of 4'-methoxy-7-O-oleoyl daizeol (I-1)

Dissolve 1.0 g (3.7 mmol) 4'-methoxy daizeol in 20 ml dichloromethane, add 2 ml anhydrous pyridine, heat to reflux of 60, add 2.24 g (7.5 mmol) oleoyl chloride for reaction for 2 h. Wash the reaction solution with diluted hydrochloric acid for three times, dry with anhydrous sodium sulfate in organic phase and stay overnight. Remove the solvent by concentrating, recrystallize the crude product with anhydrous ethanol and obtain 1.81 g white fine granular solid (I-1) with the productivity of 92%, mp 76-80.

IR (KBr) 1743 cm$^{-1}$, 1645 cm$^{-1}$ $^1$H-NMR (CDCl$_3$) δ0.88 (t, 3H —CH$_3$), δ2.60 (t 2H —CO—CH$_2$—), δ3.84 (s 3H —OCH$_3$), δ5.37 (m 2H —CH=CH—), δ7.15 (dd 1H C6-H), δ7.28 (d 1H C8-H), δ7.97 (s 1H C2-H), δ8.31 (d 1H C5-H)

MS (EI) m/e: 532.

Elementary analysis: C$_{34}$H$_{44}$O$_5$ theory: C, 76.66% H, 8.32%; actual measurement: C, 76.22% H, 8.03%.

Embodiment 3

Preparation of 4'-methoxy-7-O-linoleoyl daizeol (I-2)

Add 2.22 g (7.5 mmol) linoleoyl chloride and obtain 1.13 g white fine granular solid (I-2) by means of the method similar to the compound (I-1) with the productivity of 57%, mp 68-74.

IR (KBr) 1761 cm$^{-1}$, 1638 cm$^{-1}$ $^1$H-NMR (CDCl$_3$) δ0.88 (t, 3H —CH$_3$), δ2.60 (t 2H —CO—CH$_2$—), δ3.85 (s 3H —OCH$_3$), δ7.14 (dd 1H C6-H), δ7.28 (d 1H C8-H), δ7.97 (s 1H C2-H), δ8.31 (d 1H C5-H)

MS (EI) m/e: 530

Elementary analysis: C$_{34}$H$_{42}$O$_5$·0.5H$_2$O theory: C, 75.66% H, 8.03%; actual measurement: C, 76.08% H, 8.03%.

Embodiment 4

Preparation of 4'-methoxy-7-O-stearoyl daizeol (I-3)

Add 2.25 g (7.5 mmol) stearyl chloride 2.25 g (7.5 mmol) and obtain 1.59 g white fine granular solid (I-3) by means of the method similar to the compound (I-1) with the productivity of 80%, mp 98-100.

IR (KBr) 1762 cm$^{-1}$, 1638 cm$^{-1}$ $^1$H-NMR (CDCl$_3$) δ0.88 (t, 3H —CH$_3$), δ2.61 (t 2H —CO—CH$_2$—), δ3.85 (s 3H —OCH$_3$), δ7.15 (dd 1H C6-H), δ7.29 (d 1H C8-H), δ7.98 (s 1H C2-H), δ8.31 (d 1H C5-H)

MS (EI) m/e: 534

Elementary analysis: $C_{34}H_{46}O_5 \cdot 0.5H_2O$ theory: C, 75.10% H, 8.71%; actual measurement: C, 75.08% H, 8.78%.

Embodiment 5

Preparation of 4'-methoxy-7-O-palmityl daizeol (I-4)

Add 2.05 g (7.5 mmol) palmitoyl chloride 2.05 g (7.5 mmol) and obtain 1.38 g white filament crystal (I-4) by means of the method similar to the compound (I-1) with the productivity of 73%, mp 102-104.

IR (KBr) 1763 cm$^{-1}$, 1638 cm$^{-1}$ $^1$H-NMR (CDCl$_3$) $\delta$0.92 (t, 3H —CH$_3$), $\delta$2.65 (t 2H —CO—CH$_2$—), $\delta$3.89 (s 3H —OCH$_3$), $\delta$7.19 (dd 1H C6-H), $\delta$7.32 (d 1H C8-H), $\delta$8.02 (s 1H C2-H), $\delta$8.35 (d 1H C5-H)

MS (EI) m/e: 506

Elementary analysis: $C_{32}H_{42}O_5$ theory: C, 75.86% H, 8.35%; actual measurement: C, 75.90% H, 8.67%

Embodiment 6

Preparation of 4'-methoxy-7-O-undecylenoyl daizeol (I-5)

Add 1.51 g (7.5 mmol) undecylenylacyl chloride 1.51 g (7.5 mmol) and obtain 1.07 g white flasky crystal (I-5) with the productivity of 66%, mp 79-82.

IR (KBr) 1744 cm$^{-1}$, 1646 cm$^{-1}$ $^1$H-NMR (CDCl$_3$) $\delta$2.60 (t 2H —CO—CH$_2$—), $\delta$3.83 (s 3H —OCH$_3$), $\delta$4.95 (dd 2H CH$_2$=), $\delta$5.82 (m 1H —CH=), $\delta$7.14 (dd 1H C6-H), $\delta$7.27 (d 1H C8-H), $\delta$7.96 (s 1H C2-H), $\delta$8.30 (d 1H C5-H)

MS (EI) m/e: 434

Elementary analysis: $C_{27}H_{30}O_5$ theory: C, 74.63% H, 6.96%; actual measurement: C, 74.53% H, 6.93%

Embodiment 7

Preparation of 7-methoxy daizeol

Dissolve 9.00 g (59.0 mmol) hydroxyphenylacetic acid with 36 ml freshly distilled boron trifluoride diethyl etherate solution and then add 9.6 ml (88.0 mmol) m-methoxyphenol. The mixture reacts for 3 h at 102° C. Slowly pour the mixture into 150 ml saturated bicarbonate solution, stir vigorously, filter out the precipitated red solid, recrystallize with anhydrous ethanol and obtain 7.52 g off-white powder of 2-hydroxyl-4-methoxy-4'-hydroxyl deoxybenzoin with the productivity of 48.6%, mp 150-152, MS (EI) m/e: 258.

Take 6.00 g (23.0 mmol) product of above step and 8.00 g (67.0 mmol) DMF-DMA (N,N-dimethylformamide dimethyl acetal) dissolved in 20 ml anhydrous toluene, heat to reflux for 2 h, statically cool down to precipitate the solid. Recrystallize the crude product with absolute methanol after filtration and obtain 5.11 g faint yellow product of 7-methoxy daizeol with the productivity of 82%, mp 215-218.

MS (ESI) m/e: 269 [M+H]$^+$

Embodiment 8

Preparation of 7-methoxy-4'-O-oleoyl daizeol (II-1)

Dissolve 1.0 g (3.7 mmol) 7-methoxy daizeol in 20 ml dichloromethane, add 2 ml anhydrous pyridine, heat to reflux of 60° C., add 2.24 g (7.5 mmol) oleoyl chloride for reaction for 2 h. Wash the reaction solution with diluted hydrochloric acid for three times, dry with anhydrous sodium sulfate in organic phase and stay overnight. Remove the solvent by concentrating, recrystallize the crude product with anhydrous ethanol and obtain 1.61 g white fine granular solid (II-1) with the productivity of 81%, mp 76-78.

IR (KBr) 1746 cm$^{-1}$, 1639 cm$^{-1}$ $^1$H-NMR (CDCl$_3$) $\delta$0.88 (t, 3H —CH$_3$), $\delta$2.56 (t 2H —CO—CH$_2$—), $\delta$3.92 (s 3H —OCH$_3$), $\delta$5.36 (m 2H —CH=CH—), $\delta$6.85 (d 1H C8-H), $\delta$6.99 (dd 1H C6-H), $\delta$7.94 (s 1H C2-H), $\delta$8.21 (d 1H C5-H)

MS (EI) m/e: 532

Elementary analysis: $C_{34}H_{44}O_5$ theory: C, 76.66% H, 8.32%; actual measurement: C, 76.86% H, 8.48%

Embodiment 9

Preparation of 7-methoxy-4'-O-linoleoyl daizeol (II-2)

Add 2.22 g (7.5 mmol) linoleoyl chloride and obtain 1.36 g white fine granular solid (II-2) by means of the method similar to the compound (I-1) with the productivity of 69%, mp 58-62.

IR (KBr) 1746 cm$^{-1}$, 1639 cm$^{-1}$ $^1$H-NMR (CDCl$_3$) $\delta$0.88 (t, 3H —CH$_3$), $\delta$2.56 (t 2H —CO—CH$_2$—), $\delta$3.90 (s 3H —OCH$_3$), $\delta$6.85 (d 1H C8-H), $\delta$6.99 (dd 1H C6-H), $\delta$7.93 (s 1H C2-H), $\delta$68.21 (d 1H C5-H)

MS (EI) m/e: 530

Elementary analysis: $C_{34}H_{42}O_5$ theory: C, 76.95% H, 7.98%; actual measurement: C, 76.64% H, 8.02%

Embodiment 10

Preparation of 7-methoxy-4'-O-stearoyl daizeol (II-3)

Add 2.25 g (7.5 mmol) stearyl chloride 2.25 g and obtain 1.69 g white fine granular solid (II-3) by means of the method similar to the compound (II-1) with the productivity of 85%, mp 98-102.

IR (KBr) 1746 cm$^{-1}$, 1639 cm$^{-1}$ $^1$H-NMR (CDCl$_3$) $\delta$0.88 (t, 3H —CH$_3$), $\delta$2.57 (t 2H —CO—CH$_2$—), $\delta$3.92 (s 3H —OCH$_3$), $\delta$6.87 (d 1H C8-H), $\delta$7.00 (dd 1H C6-H), $\delta$7.95 (s 1H C2-H), $\delta$8.21 (d 1H C5-H)

MS (EI) m/e: 534

Embodiment 11

Preparation of 7-methoxy-4'-O-palmityl daizeol (II-4)

Add 2.05 g (7.5 mmol) palmitoyl chloride and obtain 1.72 g white solid (II-4) by means of the method similar to the compound (II-1) with the productivity of 91%, mp 96-100.

IR (KBr) 1745 cm$^{-1}$, 1638 cm$^{-1}$ $^1$H-NMR (CDCl$_3$) $\delta$0.88 (t, 3H —CH$_3$), $\delta$2.56 (t 2H —CO—CH$_2$—), $\delta$3.92 (s 3H —OCH$_3$), $\delta$6.86 (d 1H C8-H), $\delta$7.00 (dd 1H C6-H), $\delta$7.94 (s 1H C2-H), $\delta$8.21 (d 1H C5-H)

MS (EI) m/e: 506

Embodiment 12

Preparation of 7-methoxy-4'-O-undecylenoyl daizeol (II-5)

Add 1.51 g (7.5 mmol) undecylenylacyl chloride and obtain 1.21 g white solid (II-5) by means of the method similar to the compound (II-1) with the productivity of 75%, mp 88-90.

IR (KBr) 1746 cm$^{-1}$, 1639 cm$^{-1}$ $^1$H-NMR (CDCl$_3$) $\delta$2.56 (t 2H —CO—CH$_2$—), $\delta$3.92 (s 3H —OCH$_3$), $\delta$4.96 (dd 2H CH$_2$=), $\delta$5.81 (m 1H —CH=), $\delta$6.86 (d 1H C8-H), $\delta$7.00 (dd 1H C6-H), $\delta$7.94 (s 1H C2-H), $\delta$8.21 (d 1H C5-H)

MS (EI) m/e: 434

Elementary analysis: $C_{27}H_{30}O_5$ theory: C, 74.63% H, 6.96%; actual measurement: C, 74.63% H, 7.04%

Embodiment 13

Preparation of 3',4'-dimethoxy daizeol

Dissolve 3.6 g resorcin (32.5 mmol) with 50 ml freshly distilled boron trifluoride diethyl etherate solution and then add 5.88 g (30.0 mmol) 3,4-dimethoxyphenylacetic acid. The mixture reacts for 1 h at 100° C. Add 100 ml diethyl ether for dilution after cooling, extract three times with saturated sodium bicarbonate solution, add anhydrous sodium sulfate in organic phase and dry for a night. Remove the solvent by reducing pressure and concentrating, recrystallize the crude product with anhydrous ethanol and obtain 6.0 g off-white power with the productivity of 70%, mp 150-154, MS (EI) m/e: 289[M+H]$^+$.

Take 5.76 g (20 mmol) product of above step and 4.8 g (40.0 mmol) DMF-DMA (N,N-dimethylformamide dimethyl acetal) dissolved in 60 ml anhydrous toluene, heat to reflux for 2 h, statically cool down to precipitate the solid. Recrystallize with 95% ethanol after filtration and obtain 4.0 g faint yellow product of 3',4'-dimethoxy daizeol with the productivity of 67%, mp 258-260. MS (ESI) m/e: 299 [M+H]$^+$.

Embodiment 14

Preparation of 3',4'-dimethoxy-7-O-oleoyl daizeol (I-6)

Dissolve 1.1 g (3.7 mmol) 3',4'-dimethoxy daizeol in 20 ml dichloromethane, add 2 ml anhydrous pyridine, heat to reflux of 60° C., add 2.24 g (7.5 mmol) oleoyl chloride for reaction for 2 h. Wash the reaction solution with diluted hydrochloric acid for three times, dry with anhydrous sodium sulfate in organic phase and stay overnight. Remove the solvent by concentrating, recrystallize the crude product with anhydrous ethanol and obtain 1.6 g white fine granular solid (I-6) with the productivity of 77%, mp 74-76.

IR (KBr) 1745 cm$^{-1}$, 1645 cm$^{-1}$ $^1$H-NMR (CDCl$_3$) δ0.88 (t, 3H —CH$_3$), δ2.60 (t 2H —CO—CH$_2$—), δ3.85 (s 6H —OCH$_3$), δ5.37 (m 2H —CH=CH—), δ7.17 (dd 1H C6-H), δ7.30 (d 1H C8-H), δ8.01 (s 1H C2-H), δ8.30 (d 1H C5-H)

MS (EI) m/e: 562

Elementary analysis: C$_{35}$H$_{46}$O$_6$ theory: C, 74.70% H, 8.24%; actual measurement: C, 74.67% H, 8.25%

Embodiment 15

Take 25 g compound prepared in Embodiment 2 and 35 g soybean oil, mix them uniformly into encapsulated liquid, prepare the capsule shell liquid by conventional method and suppress to make soft capsule.

What is claimed is:

1. A compound of the following formula I or II

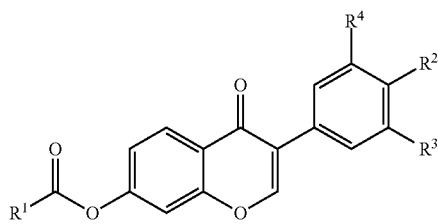

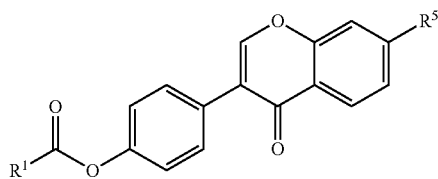

$R^1$ represents: $C_{11}$-$C_{30}$ fatty alkyl groups;

$R^2$ represents H, OH, OR', SR', NHR', N(CH$_3$)$_2$, NO$_2$, halogen, CF$_3$ or C(O)R' respectively, $R^3$ represents H, OR', SR', NHR', N(CH$_3$)$_2$, NO$_2$, halogen, CF$_3$ or C(O)R' respectively and $R^4$ represents H, OR', SR', NHR', N(CH$_3$)$_2$, NO$_2$, halogen, CF$_3$ or C(O)R' respectively, in which R' represents C$_1$-C$_4$ alkyl group and when $R^3$ and $R^4$ represent H $R^2$ does not represent OH;

$R^5$ represents H, OR', SR', NHR', N(CH$_3$)$_2$, NO$_2$, halogen, CF$_3$ or C(O)R', in which R' represents C$_1$-C$_4$ alkyl group;

when $R^4$ represents H, $R^2$ and $R^3$ can form

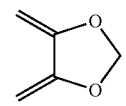

with their combined carbon atom.

2. The compound according to claim 1, wherein $R^1$CO represents a fatty acyl group formed by oleic acid, linoleic acid, undecylenic acid, linolenic acid, conjugated linoleic acid, stearic acid, palmitoleic acid, eicosatetraenoic acid, eicosapentaenoic acid, eicosenoic acid, docosahexaenoic acid, lauric acid, capric acid, octanoic acid or hydroxy-2-decenoic acid after removal of hydroxide radical.

3. The compound according to claim 2, wherein $R^1$CO represents oleoyl, linoleoyl, linolenic acyl, conjugated linoleoyl or palmitoleic acyl.

4. The compound according to claim 1, wherein $R^2$ represents H, OH, OCH$_3$, SCH$_3$, NHCH$_3$, N(CH$_3$)$_2$, NO$_2$, halogen, CF$_3$ or C(O)CH$_3$.

5. The compound according to claim 4, wherein $R^2$ represents OCH$_3$.

6. The compound according to claim 1, wherein $R^3$ or $R^4$ represents H or OCH$_3$.

7. The compound according to claim 1, wherein for formula II $R^5$ represents H, OCH$_3$, SCH$_3$, NHCH$_3$, N(CH$_3$)$_2$, NO$_2$, halogen, CF$_3$ or C(O)CH$_3$.

8. The compound according to claim 7, wherein $R^5$ represents OCH$_3$.

9. A pharmaceutical composition comprising the compound of claim 1 and a pharmaceutically acceptable carrier.

10. A method for treating hyperlipidemia, obesity or type II diabetes, comprising administering an effective amount of the pharmaceutical composition of claim 9 to a person suffering from hyperlipidemia, obesity or type II diabetes.

* * * * *